United States Patent
Gupta et al.

(10) Patent No.: US 8,951,577 B2
(45) Date of Patent: Feb. 10, 2015

(54) ANTIMICROBIAL HYDROCHLORIC ACID CATHETER LOCK SOLUTION AND METHOD OF USE

(75) Inventors: Nisha Gupta, Audobon, PA (US);
Elaine Steinke, Morgantown, PA (US);
Joel Rosenblatt, Pottstown, PA (US)

(73) Assignee: Teleflex Medical Incorporated, Durham, NC (US)

( * ) Notice: Subject to any disclaimer, the term of this patent is extended or adjusted under 35 U.S.C. 154(b) by 453 days.

(21) Appl. No.: 12/849,665

(22) Filed: Aug. 3, 2010

(65) Prior Publication Data

US 2012/0034319 A1 Feb. 9, 2012

(51) Int. Cl.
| | | |
|---|---|---|
| A01N 59/00 | (2006.01) |
| A61K 33/18 | (2006.01) |
| A61L 29/16 | (2006.01) |
| A61L 2/00 | (2006.01) |
| A61L 29/14 | (2006.01) |
| A61K 31/18 | (2006.01) |
| A61K 31/727 | (2006.01) |

(52) U.S. Cl.
CPC . *A61L 29/16* (2013.01); *A61L 2/00* (2013.01); *A61L 29/14* (2013.01); *A61K 31/18* (2013.01); *A61K 31/727* (2013.01)
USPC ........................................ 424/666

(58) Field of Classification Search
None
See application file for complete search history.

(56) References Cited

U.S. PATENT DOCUMENTS

| | | | |
|---|---|---|---|
| 6,423,050 B1 | 7/2002 | Twardowski | |
| 6,527,979 B2 * | 3/2003 | Constantz et al. | 252/364 |
| 2004/0232381 A1 | 11/2004 | Pinza et al. | |
| 2009/0192165 A1 | 7/2009 | Burwell et al. | |
| 2009/0192231 A1 * | 7/2009 | Lemons | 514/738 |
| 2010/0055086 A1 | 3/2010 | Raad | |
| 2010/0191219 A1 | 7/2010 | Gupta et al. | |

FOREIGN PATENT DOCUMENTS

| | | |
|---|---|---|
| JP | 2002336362 A | 11/2002 |
| JP | 2005527302 A | 9/2005 |
| JP | 2006305375 A | 11/2006 |
| JP | 2009249345 A | 10/2009 |
| JP | 2010178786 A | 8/2010 |

OTHER PUBLICATIONS

Shulman et al., J Parenter Enteral Nutr 12 509 1988 (Abstract).*
Schulman et al., "Use of Hydrochloric Acid to Clear Obstructed Central Venous Catheters," J Parent Ent Nutrition 12: 509-510 (1988)—entire article.*
International Search Report and Written Opion for PCT/US11/40119, completed Oct. 12, 2011.
Barbaric, D. et al., "Role of Hydrochloric Acid in the Treatment of Central Venous Catheter Infections in Children with Cancer", Cancer, 2004 American Cancer Society, vol. 101, No. 8, pp. 1866-1872.

* cited by examiner

*Primary Examiner* — Robert A Wax
*Assistant Examiner* — Thor Nielsen
(74) *Attorney, Agent, or Firm* — Baker & Hostetler LLP

(57) ABSTRACT

A catheter lock solution includes a hydrochloric acid solution having a concentration of 0.3 Molar to 1.0 Molar. This hydrochloric acid solution may be used to lock a catheter and/or salvage an infected catheter.

44 Claims, 4 Drawing Sheets

ANTIMICROBIAL HYDROCHLORIC ACID CATHETER LOCK SOLUTION AND METHOD OF USE

FIELD OF THE INVENTION

The present invention generally relates to a solution for use in a medical catheter. More particularly, the present invention pertains to an antimicrobial hydrochloric acid solution for use in a medical catheter and a method of use thereof.

BACKGROUND OF THE INVENTION

Catheters are presently utilized in a great variety of medical procedures where they provide a great benefit to patients and medical practitioners. Unfortunately, conventional catheters are capable of being contaminated with microorganisms. Catheter-related infections are thought to arise by several different mechanisms. Contamination of the catheter hub and subsequent colonization of catheters by microbes as well as formation of a bacterial biofilm on the external and internal surfaces are thought to be the major routes for catheter related infections. Many catheter related blood stream infections (CRBSI) are derived from intraluminal contaminants. To address this problem, catheter lumens can be locked with an antimicrobial solution. For the purposes of this disclosure, the term, "locked" refers to filling the catheter lumen with a solution that is allowed to dwell or remain in place for at least a minute. Catheter lock solutions containing salts of citrate, ethanol, ethylenediaminetetraacetic acid (EDTA), antibiotics and methylene blue are generally known. See: 1) Garland J. S., Alex C. P., Henrickson K. J., McAuliffe T. L., and Maki D. G. (2005) A vancomycin-heparin lock solution for prevention of nosocomial bloodstream infection in critically ill neonates with peripherally inserted central venous catheters: a prospective, randomized trial. *Pediatrics* 116: e198-205; 2) Weijmer M. C., Van den Dorpel M. A., Van de Ven P. J. G. (2005) Randomized, Clinical Trial Comparison of Trisodium Citrate 30% and Heparin as Catheter-Locking Solution in Hemodialysis Patients. *J Am Soc Nephrol* 16: 2769-2777; 3) Ash S. R. (2005) Method of enhancing catheter patency using a citrate salt catheter lock solution. United States Patent Application US20050215978A1; 4) Ash S. R. (2000) Method of enhancing catheter patency using a citrate salt catheter lock solution. International Patent WO 00/10385 A1; and 5) Opilla M. T., Kirby D. F., and Edmond M. B. (2007) Use of ethanol lock therapy to reduce the incidence of catheter-related bloodstream infections in home parenteral nutrition patients. *JPEN J Parenter Enteral Nutr.* 31: 302-305. Most of these conventional lock solutions have shown benefit in reduction of CRBSI when these solutions were allowed to dwell for extended periods, e.g., while the lumen was not in use.

The composition of a bacteriostatic lock solution containing glycerol and saline is known. The glycerol lock can be utilized as a preventive lock for long term application as it causes bacterial stasis on short term exposure but only killing of bacteria on extended exposure. The present invention relates to the composition of an antimicrobial catheter lock solution which is fast acting (e.g., less than 1 hour) and therefore can be used as a salvage lock when infection symptoms are present and a contaminated catheter is suspected. A recent clinical trial on 50% ethanol lock solution where locking was performed from 1-3 hours showed no reduction in infection relative to heparin locking (Crnich C. J., Duster M., Jones A., and Maki D. G. Prospective Randomized Double-Blind Trial of an Ethanol Lock for Prevention of CLABSI. *Proceedings 49th Interscience Conference on Antimicrobial Agents and Chemotherapy,* San Francisco, Calif. Sep. 12-16, 2009.). Thus, there still remains a need for a safe lock that can eradicate bacteria and preformed biofilms rapidly.

Accordingly, it is desirable to provide a catheter lock solution having antimicrobial properties that is capable of overcoming the disadvantages described herein at least to some extent.

SUMMARY OF THE INVENTION

The foregoing needs are met, to a great extent, by the present invention, wherein in one respect a catheter lock solution having antimicrobial properties, a catheter lock solution kit, and a method of use with a catheter is provided.

An embodiment of the present invention pertains to a catheter lock solution in a catheter. The catheter lock solution includes a hydrochloric acid solution having a concentration of 0.3 Molar to 1.0 Molar.

Another embodiment of the present invention relates to a catheter salvage solution in a catheter. The catheter salvage solution includes a hydrochloric acid solution having a concentration of 0.3 Molar to 1.0 Molar.

Yet another embodiment of the present invention pertains to a method of inhibiting microbial contamination in a catheter. In this method a lumen of the catheter is infused with a hydrochloric acid solution having a concentration of 0.3 Molar to 1.0 Molar.

Yet another embodiment of the present invention relates to a method of treating a patient having a microbial contamination of an indwelling catheter. In this method a lumen of the catheter is infused with a hydrochloric acid solution having a concentration of 0.3 Molar to 1.0 Molar.

Yet another embodiment of the present invention pertains to a catheter kit includes a catheter and a hydrochloric acid solution having a concentration of 0.3 Molar to 1.0 Molar.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

Figure 1:
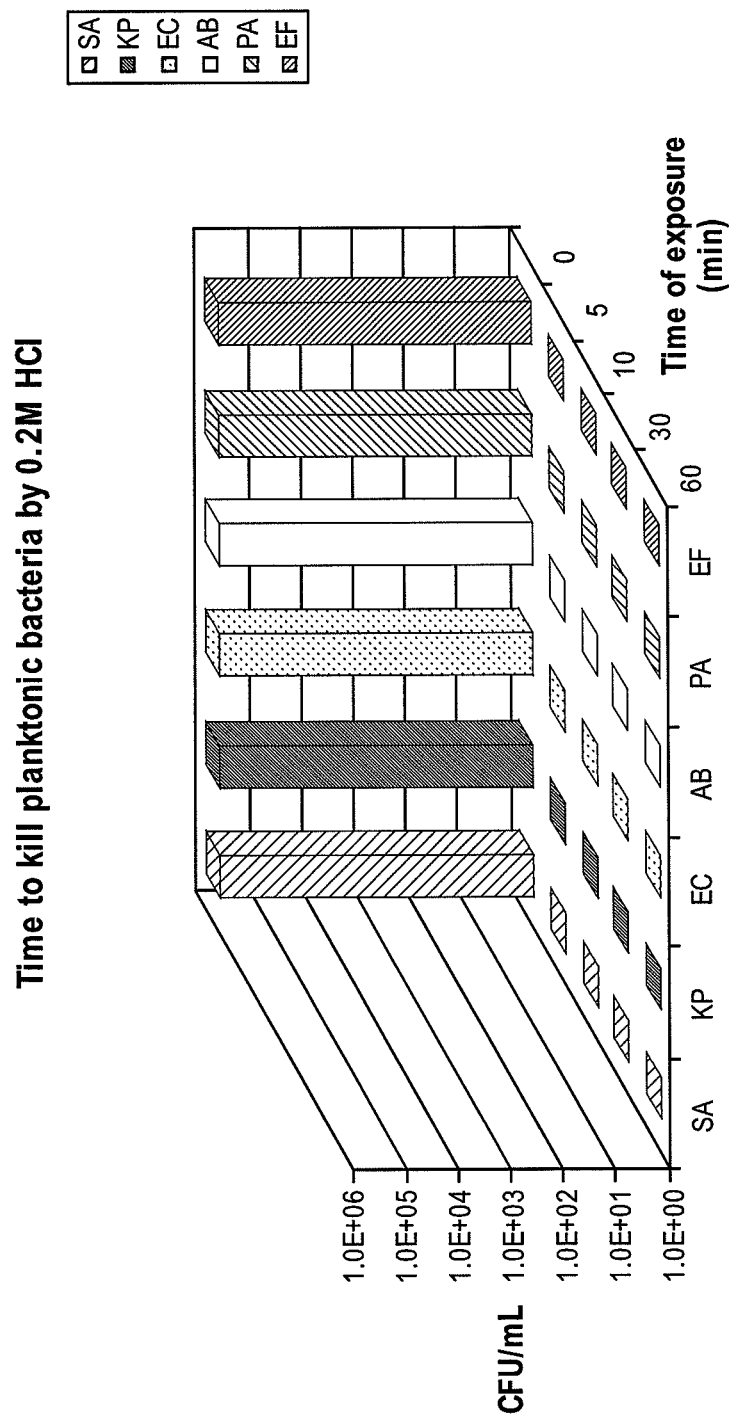
FIG. 1 is a graph showing the effect of 0.2 M HCl on various bacterial strains in planktonic suspensions.

Embodiments of the invention provide a hydrochloric acid (HCl) catheter lock solution, a HCl catheter salvage solution, a method of inhibiting microbial growth in a catheter, and a method of treating a patient having a microbial contamination of an indwelling catheter, and a catheter kit. In various embodiments, the HCl catheter lock solution and/or HCl catheter salvage solution may have any suitable concentration. In general, examples of suitable concentrations include those concentrations capable of antibacterial properties either alone or in combination with other agents. Particular examples of suitable HCl concentrations include between 0.3 molar (M) to 1M. In other examples shown herein, concentrations of HCl as low as 0.001 M either alone or in combination with another agent may be suitable for use as an antibiotic catheter lock and/or salvage solution. Furthermore, HCl concentrations greater than 1 M may also be suitable for use as an antibiotic catheter lock and/or salvage solution.

In a particular example, the catheter lock and/or salvage solution disclosed here contains between 0.3M-1M HCl. At this concentration range HCl can kill both bacteria and yeast in less than 60 minutes and has no systemic effect if accidentally flushed due to rapid neutralization by phosphate in blood. In the event of leakage or accidental flush of this lock solution in the blood stream the local pH remains in the physiological range i.e. at pH 7.38-7.42. Unlike the other antimicrobial lock solutions described before, the HCl catheter lock and/or salvage solution described in this invention is fast acting requiring a dwelling period of less than an hour, thus can be utilized as an effective catheter salvage solution when catheter infection is suspected.

In addition to HCl, it is within the purview of this and other embodiments of the invention that other suitable agents may be incorporated into the catheter lock and/or salvage solution. Examples of suitable agents includes other antibiotics, antiseptics, antimicrobial peptides, antithrombogenics, fibrinolytics, anticoagulants (particularly heparin), anti-inflammatory agents, anti-pain agents, vasodilators, antiproliferatives, antifibrotics, growth factors, cytokines, antibodies, peptides and peptide mimetics, nucleic acids, and/or the like.

Medical devices suitable for use with various embodiments of the invention may include catheters, tubes, etc. Other devices suitable for use with embodiments of the invention include those that would benefit from having a broad spectrum of antimicrobial and/or antifungal activity such as devices that interface with blood, blood products, and/or fibrinogenic fluids, tissues, and/or products.

Methods

Experiment 1

Preparation of Catheter Lock/Salvage Solutions

A stock solution of 2M HCl was purchased from Fisher Scientific of Pittsburgh, Pa. 15275 U.S.A. One hundred milliliters (100 mL) of solutions each containing varying HCl concentration ranging from 0.001M-2M were prepared in deionized water as shown in Table 1 below:

TABLE 1

| Catheter Lock/Salvage Solutions | | |
|---|---|---|
| Lock/Salvage solution | 2M HCl (mL) | Water (mL) |
| 2M HCl | 100 | 0 |
| 1M HCl | 50 | 50 |
| 0.5M HCl | 25 | 75 |
| 0.4M HCl | 20 | 80 |
| 0.3M HCl | 15 | 85 |
| 0.2M HCl | 10 | 90 |
| 0.1M HCl | 5 | 95 |
| 0.01M HCl | 0.5 | 99.5 |
| 0.001M HCl | 0.05 | 99.95 |

Experiment 2

Minimum Inhibitory Concentration (MIC)

The HCl solutions as listed in Table 1 were prepared in Muller-Hinton broth instead of water. The pH of each of the solution was measured and then tested against *Candida albicans* (*C. albicans*), *Pseudomonas aeruginosa*(*P. aeruginosa*) and *Staphylococcus aureus* (*S. aureus*) for range-finding of its MIC. The organism and the MIC of HCl for the respective organism (with corresponding pH in parenthesis) are as follows:

*C. albicans*=0.08M-0.1M HCl (pH 2.07-1.93)
*P. aeruginosa*=0.001M-0.02M (pH 7.33-4.06)
*S. aureus*=0.02M-0.04M (pH 4.06-3.12)

Experiment 3

Antimicrobial Effect of HCl on Planktonic Microorganisms as Determined by "Time to Kill" Assay Time to kill planktonic microbial cultures was determined following the exposure to either 0.1M or 0.2M HCl. The cultures included six bacterial and one yeast. The six bacterial strains tested were: 1) *S. aureus* "SA"; 2) *Klebsiella pneumoniae* "KP"; 3) *Escherichia coli* "EC"; 4) *Acinetobacter baumannii* "AB"; 5) *P. aeruginosa* "PA"; and 6) Vancomycin-resistant *Enterococcus faecalis* "EF". The yeast tested was *Candida albicans* "CA". The time of exposure for the planktonic microbial cultures was for 5, 10, 30 and 60 minutes.

Briefly, the procedure for time to kill planktonic bacteria assay is as follows—wells of 48-well plates were filled with 1 mL each of the HCl solutions or the control solution which is 0.85% saline, followed by addition of $10^6$ colony forming units per milliliter (CFU/mL) of a test organism. Subsequently, an aliquot of 10 microliters (μL) from each well was removed every 5, 10, 30, 60 minutes and serially diluted in phosphate buffered saline (PBS). Ten (10) μl of each dilution was then plated onto the surface of Dey/Engley (D/E) Neutralizing Agar. Plates were inverted and incubated at 37 degrees Celsius (° C.) for 24 hours. Subsequently number of colonies per plate was recorded and CFU/mL was determined. Each test was run in triplicate.

Results from the testing of 0.2M HCl are shown in FIG. 1. As shown in FIG. 1, all six bacterial strains tested were killed within 10 minutes of exposure to 0.1M HCl.

Figure 2:
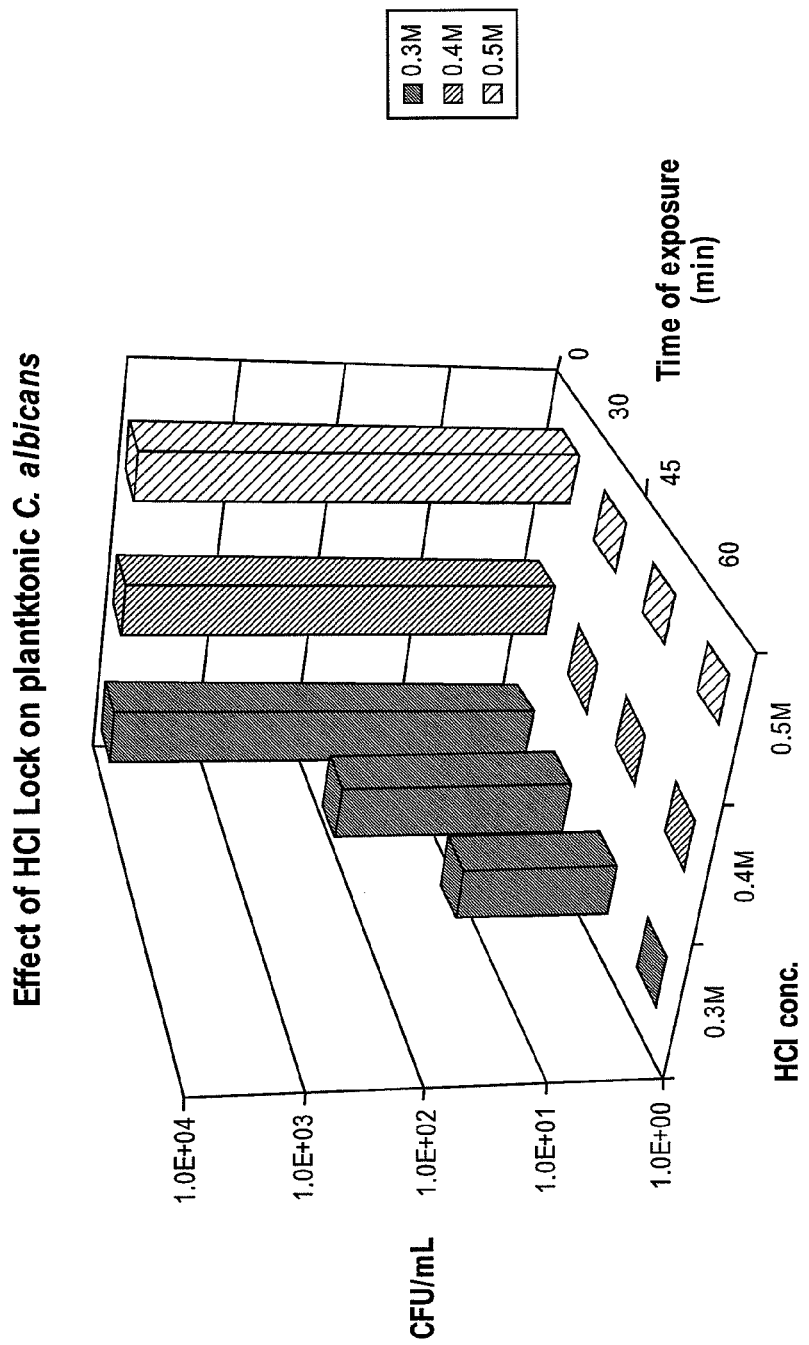
FIG. 2 is a graph showing the effect of various concentrations of HCl on *Candida albicans* in planktonic suspension.

Although not shown in FIG. 1, *C. albicans* was tested in the same manner as the bacterial samples. While exposure to 0.2 M HCl killed planktonic bacteria essentially instantly, approximately 2 hours of exposure was required to kill planktonic *C. albicans* at 0.2M HCl. By increasing the HCl concentration to 0.4M as shown in FIG. 2, the time to kill planktonic *C. albicans* was reduced to 30 minutes.

Experiment 4

Figure 3:
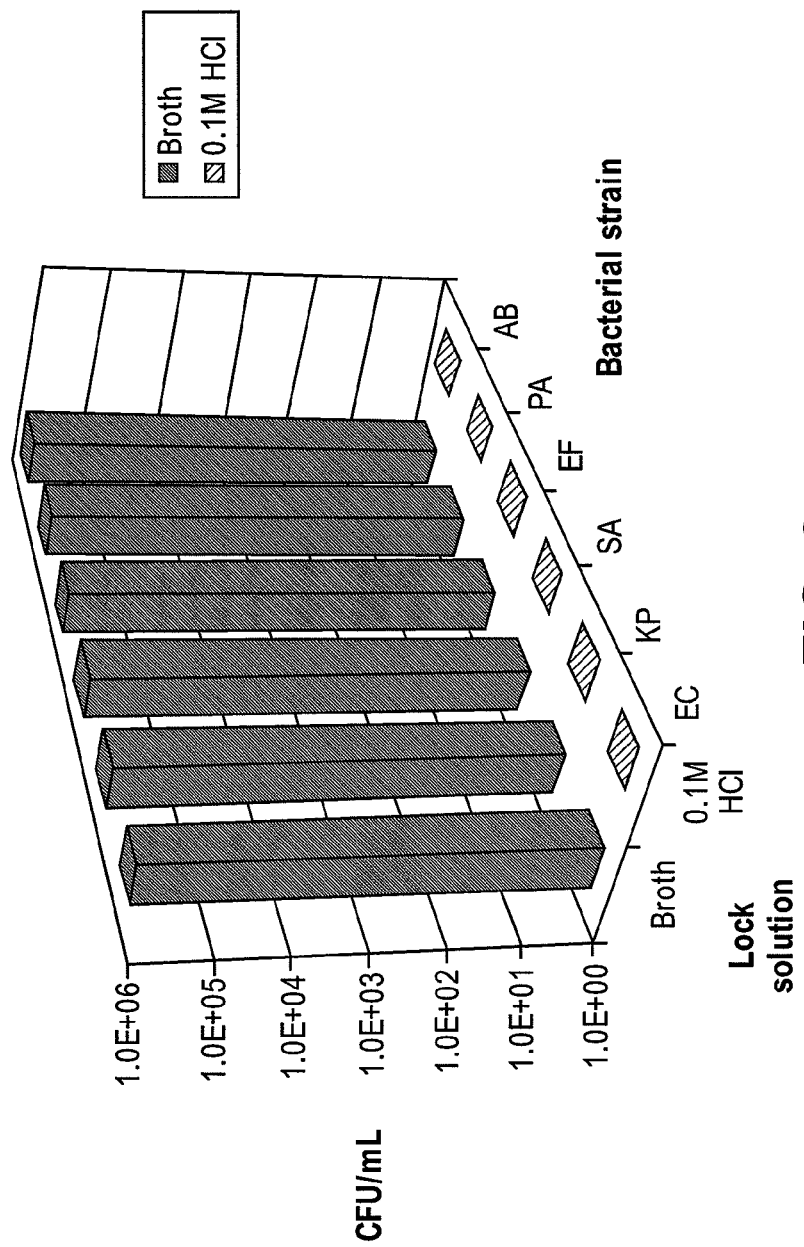
FIG. 3 is a graph showing the effect of 0.1 M HCl on various bacterial strains in pre-formed bacterial biofilms.
Figure 4:
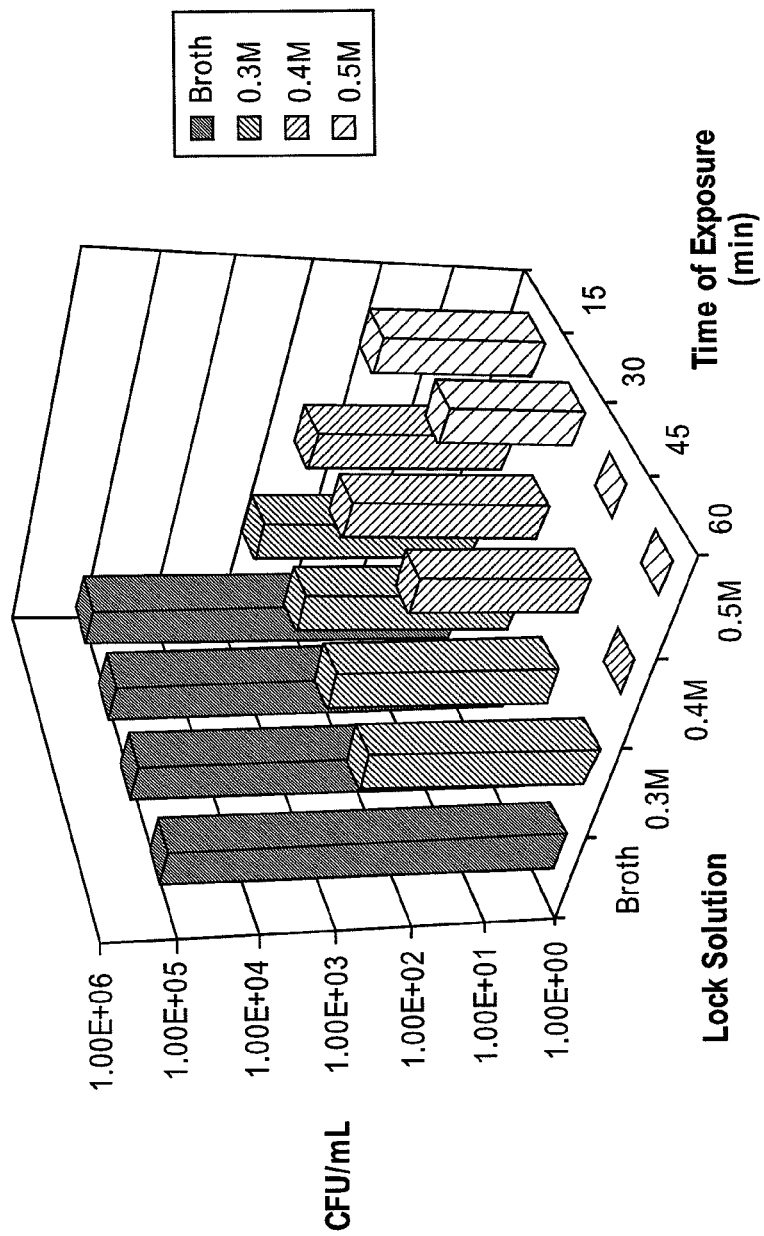
FIG. 4 is a graph showing the effect of various concentrations of HCl on *Candida albicans* in pre-formed bacterial biofilms over time.

Antimicrobial Effect of HCl as Determined by Time to Eradicate Pre-Formed Biofilm Pre-formed biofilm of *E. coli* "EC", *K. pneumoniae* "KP", *S. aureus* "SA", Vancomycin-resistant *E. faecalis* "EF", *P. aeruginosa* "PA", *A. baumanii* "AB", and *C. albicans* "CA" were exposed to either broth, saline, or solutions containing 0.1M-0.5M HCl for 5-60 minutes. The procedure to determine time to eradicate pre-formed biofilms is as follows: half a centimeter segments were cut from sterile 14 French Gauge (Fr) double lumen CARBOTHANE® extrusions (CARBOTHANE® is a thermoplastic polycarbonate and is a registered Trademark of Lubrizol Advanced Materials, Inc. of Wickliffe, Ohio 44092, U.S.A.). In a 48 well micro-titer plate (one per organism), wells were filled with either 1 mL of Trypticase Soy Broth (TSB) to grow bacteria or Yeast malt broth (YMB) for growing yeast. Subsequently, using a sterile forceps one catheter segment was placed in each well of the plate followed by addition of the organism per well. Plates were then incubated for 24 hours (hrs) at 37° C. in an incubator with shaking at 100 revolutions per minute (rpm). After 24 hrs, the catheter segments were removed from the media and placed into another 48 well plate, containing 1 ml of either TSB, YMB, saline, 0.1M, 0.2M, 0.3M, 0.4M or 0.5M HCl. At the indicated time point, the segments were removed and placed into another 48 well plate, containing 1 mL of D/E broth (Dey-Engley neutralizing broth) in each well. The 48 well plate was placed into a suitable sonication bath and sonicated for 20 minutes at approximately 50° C. Examples of suitable sonication baths include the VWR 250HT, manufactured by VWR International of West Chester, Pa. 19380 U.S.A.). Once sonication was completed, an aliquot of 10 ul was removed and serially diluted in PBS. Ten microliters (10 µl) of each dilution was then plated onto the surface of D/E Neutralizing Agar. Plates were incubated at 37° C. for 24 hrs and number of colonies per plate was recorded to determine CFU/mL. As shown in FIG. 3, all bacterial biofilm were eradicated within half an hour of exposure to 0.1M HCl. As shown in FIG. 4, yeast biofilm were eradicated in less than an hour by HCl at concentrations higher than 0.4M.

Experiment 5

Ability of HCl Lock to Salvage "Infected" Catheter

The arterial ports of 15 Fr, 19 centimeter (cm) hemodialysis catheters were locked with $10^3$ CFU of *C. albicans* in YMB (in a volume that is specified on the product as the priming volume). The catheters were incubated in sterilization pouches for 24 hours at 37° C. Thereafter, the catheters were removed from the pouches and the YMB was flushed out. Catheters were then re-locked with either YMB or HCl solutions. After an incubation period of 30 minutes, the lock solutions were removed and saved for plating on D/E agar. The catheters were cut into segments and transferred into 15 mL conical tubes containing 5 mL of D/E broth. The tubes containing the catheter segments were sonicated for 20 minutes. From each of the lock solutions and the catheter sonicate, 10 ul was removed and serially diluted in PBS. 10 µl of each dilution was then plated onto the surface of D/E Neutralizing Agar. Plates were inverted and incubated at 37° C. for 24 hours. Subsequently number of colonies per plate was recorded and CFU/mL was determined.

Within 30 minutes both 0.4 and 0.5M HCl solutions were able to eradicate *Candida* biofilm growing for 24 hours in the catheters. As shown in Table 2, both the HCl lock solution that was recovered after a treatment period of 30 minutes and the catheter segment treated with HCl lock were negative for presence of any organism.

TABLE 2

Catheter Salvage

| Test Solution | Lock solution CFU/mL | Catheter CFU/mL |
|---|---|---|
| YMB | 4.E+05 | 8.E+04 |
| 0.5M HCL | 0 | 0 |

Experiment 6

HCl Lock Prevents Microbial Migration

Both the arterial and venous ports of 15 Fr, 19 cm hemodialysis catheters were locked with either YMB or 0.5M HCl (in a volume that is specified on the product as the priming volume for each port). Catheters were then suspended for 24 hours at 37° C. in sterile 100 mL measuring cylinders that contained 20 mL of human plasma pre-inoculated with $10^5$ CFU of *C. albicans*. During the 24 hr incubation period, the plasma was kept stirring, and care was taken to prevent catheter tip from touching the bottom of the cylinder. Subsequently, the lock solutions were removed and saved for serial dilution and plating on D/E agar. The catheters were cut into segments and transferred into 15 mL conical tubes containing 5 mL of D/E broth. The tubes containing the catheter segments were sonicated for 20 minutes. From each of the lock solutions and the catheter sonicate, 10 ul was removed and serially diluted in PBS. 10 µl of each dilution was then plated onto the surface of D/E Neutralizing Agar. Plates were inverted and incubated at 37° C. for 24 hours. Subsequently number of colonies per plate was recorded and CFU/mL was determined.

The solution containing 0.5M HCl was able to prevent migration of *Candida* from the infected plasma into the catheter lumen as can be seen in Table 3 below.

TABLE 3

Inhibiting Microbial Migration

| | Number of colonies | |
|---|---|---|
| Lock Solution | Lock solution | Catheter |
| YMB | TNTC* | TNTC* |
| 0.4N HCL | 8 | 1 |
| 0.5N HCL | 0 | 1 |

*Too Numerous to Count

In a similar experiment as above, subsequent to 24 hour suspension of the locked catheters in plasma, the lock solutions from each catheter were collected and the pH measured at the tip, middle and distal location in the catheter lumen. For example, if the lock volume was 1 ml, three aliquots each of 333 µl were collected in three separate tubes pre-labeled as 'tip', 'middle' and 'distal'. Subsequently, the pH of each solution was measured.

As shown in Table 4 each HCl solution was able to maintain inhibitory pH through out the length of the locked catheter.

TABLE 4

Maintenance of Inhibiting pH Concentration

| | Test Solution | pH after 24 hr |
|---|---|---|
| 0.3N HCl | Original solution | 1.37 |
| | Solution from Distal | 1.37 |
| | Solution from Middle | 1.37 |
| | Solution from Tip | 1.39 |
| 0.4N HCl | Original solution | 1.32 |
| | Solution from Distal | 1.32 |
| | Solution from Middle | 1.32 |
| | Solution from Tip | 1.33 |
| 0.5N HCl | Original solution | 1.29 |
| | Solution from Distal | 1.29 |
| | Solution from Middle | 1.29 |
| | Solution from Tip | 1.30 |

Experiment 7

Safety of HCl Lock

The normal pH of human plasma is 7.38-7.42, a pH below 7.38 is too acidic, whereas a plasma pH above 7.42 is too alkaline (Atherton J. C. (2009) Acid-base balance: maintenance of plasma pH. *Anaesthesia and Intensive Care Med.* 10: 557-561). To determine how local pH would be affected if a portion or the entire volume of the HCl lock is inadvertently administered into the blood stream, 20 mL of un-coagulated serum was supplemented with 0, 20, 40 or 100 µL of solutions with varying HCl concentration, followed by pH measurement.

The priming volume for the 15 Fr, 24 cm CANNON® hemodialysis catheters is 5 mL of HCl and the blood serum volume in an average human is of 2.5 L. (CANNON® is a registered Trademark of Arrow International Investment Corp. of Wilmington Del. 19810, U.S.A.) Therefore the serum to HCl lock ratio would be 1:500 if the entire lock volume of 5 mL gets flushed into the blood stream. Significant drop in pH was observed at 1:500 ratio when HCl concentration was higher than 0.5M as shown in Table 5 below.

TABLE 5

Safety of HCl Lock Solution

| HCl Volume added (µL) | Serum: HCl lock ratio | 2M HCl | 1M HCl | 0.5M HCl | 0.4M HCl | 0.3M HCl |
|---|---|---|---|---|---|---|
| 0 | Serum alone | 7.42 | 7.42 | 7.42 | 7.42 | 7.42 |
| 20 | 1:1000 | 7.27 | 7.35 | 7.40 | 7.41 | 7.42 |
| 40 | 1:500 | 7.07 | 7.28 | 7.38 | 7.39 | 7.41 |
| 100 | 1:200 | 6.85 | 7.17 | 7.32 | 7.35 | 7.39 |

Experiment 8

HCl Lock Synergy with Antimicrobial Catheters and Antimicrobial Agents Coated onto Catheters Synergy of HCl with antibiotics used on antimicrobial catheters was determined by zone of inhibition (ZOI) assay. One centimeter long catheter segments were cut from Multilumen Central Venous Catheters (CVC) from Rifampin and Minocycline impregnated CVCs (Rif/Mino). Cultures of *S. aureus* and *P. aeruginosa* were started in Muller Hinton Broth. For each organism, concentration of the inoculum was adjusted to $1 \times 10^8$ CFU/ml using 0.5 McFarland standard. Muller Hinton Agar plates either without HCl or with varying HCl concentrations were prepared. The highest HCl concentration that allowed formation of a confluent lawn of organisms was 0.01M. Plates were streaked with a single organism using a sterile cotton applicator that was dipped into the broth culture. Using sterile forceps, 1 cm long catheter segments from the control and Rif/Mino catheters were vertically inserted into the agar. Plates were then incubated for 24 hours at 37° C. Each test was run in triplicate. Subsequently the zones of inhibition (ZOI) were measured, in millimeters (mm) using calipers and the three ZOI measurements for each test were averaged. Results of these tests are shown in Table 6.

TABLE 6

Synergy of dilute Hydrochloric acid with Rif/Mino catheters

| | | Avg. ZOI (mm) | |
|---|---|---|---|
| HCl Conc.(M) | HCl Alone | *S. Aureus* | *P. aeruginosa* |
| 0 | N/A | 34 | 7 |
| 0.001 | 0 | 36 | 8 |
| 0.01 | 0 | 41 | 18 |

As shown in Table 6, synergistic effects were observed against *S. aureus* and *P. aeruginosa* when HCl concentrations exceeded 0.001 M. These synergistic effects were completely unexpected at least because dilute HCl alone produces no measurable ZOI even at a concentration of 0.01 M. It is an advantage of embodiments of the invention that using an HCl lock solution in Rif/Mino catheters provides antibacterial properties even at, near, or in close proximity to the distal tip of the catheter where the lock solution comes in contact with and is diluted by bodily fluids. For example, comparing Rif/Mino catheters with and without HCl lock solution, if the HCl lock solution is initially 0.3 M HCl, enhanced antimicrobial properties may still be observed when diluted 300:1 with bodily fluids.

Experiment 9

HCl Lock Synergy with Antimicrobial Agents, Silver Sulfadiazine (SSD) and 5-Fluorouracil (5FU)

In a separate experiment to determine synergy of HCl with antimicrobial agents, Silver sulfadiazine (SSD) and 5-Fluorouracil (5FU), Fractional Inhibitory Concentration (FIC) of each compound was determined in presence of varying HCl concentration in Muller Hinton Agar by the Kirby-Bauer antibiotic testing method (also known as the disk diffusion antibiotic sensitivity testing method).

Agar plates and cultures of *S. aureus*, *P. aeruginosa*, and *Enterobacter aerogenes* (*E. aerogenes*) were set up as described in EXPERIMENT 8. Briefly, various amounts of HCl ranging from 0.0001M-0.01M were added to Muller Hinton Agar and allowed to solidify at room temperature. Cultures were diluted to $1 \times 10^8$ CFU/ml.

Stock solutions of SSD and 5FU at 256 µg/ml were prepared and diluted two fold in water to obtain a concentration range of 256 ppm-0.125 ppm. From each of the test solution, 20 µL was then dispensed over the Kirby Bauer diffusion disks. The disks were air dried for five minutes and using forceps applied over the agar plates. Plates were then incubated for 24 hours at 37° C. Subsequently the zones of inhibition were measured, in millimeters (mm) using calipers. Each test was run in triplicate.

The MIC of SSD against *P. aeruginosa* and *S. aureus* (no HCl) was determined to be 128 ppm. SSD tested at this concentration in presence of HCl, yielded further increase in zones of inhibition with increasing HCl concentration above 0.001 M as shown in Table 7 below:

TABLE 7

Synergy of dilute Hydrochloric acid with SSD (128 ppm)

| | | Avg. ZOI (mm) | |
|---|---|---|---|
| HCl Conc.(M) | HCl Alone | *S. Aureus* | *P. aeruginosa* |
| 0 | N/A | 4.5 | 1.1 |
| 0.001 | 0 | 6.4 | 1.2 |
| 0.01 | 0 | 6.1 | 2.4 |

As shown in Table 8, HCl displays a synergy with 5-FU against *S. aureus* at HCl concentrations above 0.001 M. As shown in Table 9, at a concentration of 0.01 M, HCl also enhanced inhibition of 5FU against *E. aerogenes*.

TABLE 8

Synergy of dilute Hydrochloric acid with 5-FU (8 ppm and 16 ppm) against *S. aureus*

| | | *S. Aureus* Avg. ZOI (mm) | |
|---|---|---|---|
| HCl Conc.(M) | HCl Alone | 5-FU (8 ppm) | 5-FU (16 ppm) |
| 0 | N/A | 0.0 | 10.0 |
| 0.001 | 0 | 0.0 | 11.5 |
| 0.01 | 0 | 13.8 | 21.4 |

TABLE 9

Synergy of dilute Hydrochloric acid with 5-FU (128 ppm and 256 ppm) against *E. aerogenes*

| | | *E. aerogenes* Avg. ZOI (mm) | |
|---|---|---|---|
| HCl Conc.(M) | HCl Alone | 5-FU (128 ppm) | 5-FU (256 ppm) |
| 0 | N/A | 11.15 | 16.15 |
| 0.01 | 0 | 12.35 | 18.95 |

As shown in Table 7-9, synergistic effects were observed against *S. aureus* and *P. aeruginosa* when HCl concentrations exceeded 0.001 M. These synergistic effects were completely unexpected at least because HCl alone produces no measurable ZOI even at a concentration of 0.01 M. It is an advantage of embodiments of the invention that using an HCl lock solution in conjunction with SSD and/or 5-FU provides antibacterial properties even when diluted, such as, for example by bodily fluids. SSD and/or 5-FU may be incorporated into a suitable catheter. In use, such as when installed in a patient, the antimicrobial agent may elute out of the catheter and inhibit bacterial colonization of the surface of the catheter, adjacent to, and/or in close proximity to the surface. It is an advantage of various embodiments of the invention that these antimicrobial agents work synergistically with HCl to further inhibit microbial growth.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A catheter lock solution in a catheter, the catheter lock solution comprising:
    a hydrochloric acid solution having a concentration of 0.3 Molar to 1.0 Molar; and
    an antimicrobial agent including 5-Fluorouracil, wherein the 5-Fluorouracil is eluted from the catheter and configured to provide a concentration of 8 ppm to 256 ppm of the 5-Fluorouracil adjacent to a surface of the catheter.

2. The catheter lock solution in a catheter according to claim 1, wherein the hydrochloric acid solution includes a hydrochloric acid concentration of 0.3 Molar to 0.5 Molar.

3. The catheter lock solution in a catheter according to claim 1, wherein the antimicrobial agent includes silver sulfadiazine.

4. The catheter lock solution in a catheter according to claim 3, wherein the silver sulfadiazine is eluted from the catheter and configured to provide a concentration of at least 128 parts per million (ppm) of the silver sulfadiazine adjacent to a surface of the catheter.

5. The catheter lock solution in a catheter according to claim 1, wherein the antimicrobial agent includes Rifampin and Minocycline.

6. The catheter lock solution in a catheter according to claim 1, further comprising:
    an anti-coagulant.

7. The catheter lock solution in a catheter according to claim 6, wherein the anti-coagulant is heparin.

8. A catheter salvage solution in a catheter, the catheter salvage solution comprising:
    a hydrochloric acid solution having a concentration of 0.3 Molar to 1.0 Molar; and
    an antimicrobial agent including 5-Fluorouracil, wherein the 5-Fluorouracil is eluted from the catheter and configured to provide a concentration of 8 ppm to 256 ppm of the 5-Fluorouracil adjacent to a surface of the catheter.

9. The catheter salvage solution according to claim 8, wherein the hydrochloric acid solution includes a hydrochloric acid concentration of 0.3 Molar to 0.5 Molar.

10. The catheter salvage solution in a catheter according to claim 8, wherein the antimicrobial agent includes silver sulfadiazine.

11. The catheter salvage solution in a catheter according to claim 10, wherein the silver sulfadiazine is eluted from the catheter and configured to provide a concentration of at least 128 ppm of the silver sulfadiazine adjacent to a surface of the catheter.

12. The catheter salvage solution in a catheter according to claim 8, wherein the antimicrobial agent includes Rifampin and Minocycline.

13. The catheter salvage solution in a catheter according to claim 8, further comprising:
an anti-coagulant.

14. The catheter salvage solution in a catheter according to claim 13, wherein the anti-coagulant is heparin.

15. A method of inhibiting microbial contamination in a catheter, the method comprising the step of:
infusing a lumen of the catheter with a hydrochloric acid solution having a concentration of 0.3 Molar to 1.0 Molar,
wherein the hydrochloric acid solution further includes an antimicrobial agent,
wherein the antimicrobial agent includes 5-fluorouracil, and
wherein the 5-fluorouracil is eluted from the catheter and configured to provide a concentration of 8 ppm to 256 ppm of the 5-fluorouracil adjacent to the surface of the catheter.

16. The method according to claim 15, further comprising the step of:
allowing the hydrochloric acid solution to dwell within the lumen for about an hour.

17. The method according to claim 16, further comprising the step of:
drawing the hydrochloric acid solution from the lumen following the hour dwell time.

18. The method according to claim 17, further comprising the step of:
flushing the catheter with a saline solution following the withdrawal of the hydrochloric acid solution.

19. The method according to claim 15, wherein the hydrochloric acid solution includes a hydrochloric acid concentration of 0.3 Molar to 0.5 Molar.

20. The method according to claim 15, wherein the antimicrobial agent includes silver sulfadiazine.

21. The method according to claim 20, wherein the silver sulfadiazine is eluted from the catheter and configured to provide a concentration of at least 128 ppm of the silver sulfadiazine adjacent to a surface of the catheter.

22. The method according to claim 15, wherein the antimicrobial agent includes Rifampin and Minocycline.

23. The method according to claim 15, further comprising:
an anti-coagulant.

24. The method according to claim 23, wherein the anti-coagulant is heparin.

25. A method of treating a patient having a microbial contamination of an indwelling catheter, the method comprising the steps of:
infusing a lumen of the catheter with a hydrochloric acid solution having a concentration of 0.3 Molar to 1.0 Molar,
wherein the hydrochloric acid solution further includes an antimicrobial agent,
wherein the antimicrobial agent includes 5-fluorouracil, and
wherein the 5-fluorouracil is eluted from the catheter and configured to provide a concentration of 8 ppm to 256 ppm of the 5-fluorouracil adjacent to the surface of the catheter.

26. The method according to claim 25, further comprising the step of:
allowing the hydrochloric acid solution to dwell within the lumen for about 30 minutes.

27. The method according to claim 26, further comprising the step of:
drawing the hydrochloric acid solution from the lumen following the hour dwell time.

28. The method according to claim 27, further comprising the step of:
flushing the catheter with a saline solution following the withdrawal of the hydrochloric acid solution.

29. The method according to claim 25, wherein the hydrochloric acid solution includes a hydrochloric acid concentration of 0.3 Molar to 0.5 Molar.

30. The method according to claim 25, further comprising the step of:
selecting a hydrochloric acid concentration of 0.4 Molar to 1.0 Molar in response to a biofilm of microbial contamination being present in the catheter.

31. The method according to claim 25, wherein the antimicrobial agent includes silver sulfadiazine.

32. The method according to claim 31, wherein the silver sulfadiazine is eluted from the catheter and configured to provide a concentration of at least 128 ppm of the silver sulfadiazine adjacent to a surface of the catheter.

33. The method according to claim 25, wherein the antimicrobial agent includes Rifampin and Minocycline.

34. The method according to claim 25, further comprising:
an anti-coagulant.

35. The method according to claim 34, wherein the anti-coagulant is heparin.

36. A catheter kit comprising:
a catheter;
a hydrochloric acid solution having a concentration of 0.3 Molar to 1.0 Molar; and
an antimicrobial agent including 5-Fluorouracil, wherein the 5-Fluorouracil is eluted from the catheter and configured to provide a concentration of 8 ppm to 256 ppm of the 5-Fluorouracil adjacent to a surface of the catheter.

37. The catheter kit according to claim 36, further comprising:
a syringe configured to mate with a port of the catheter, the syringe including the hydrochloric acid solution.

38. The catheter kit according to claim 36, further comprising:
a saline solution.

39. The catheter kit according to claim 36, wherein the hydrochloric acid solution includes a hydrochloric acid concentration of 0.3 Molar to 0.5 Molar.

40. The catheter kit according to claim 36, wherein the antimicrobial agent includes silver sulfadiazine.

41. The catheter kit according to claim 40, wherein the silver sulfadiazine is eluted from the catheter and configured to provide a concentration of at least 128 ppm of the silver sulfadiazine adjacent to a surface of the catheter.

42. The catheter kit according to claim 36, wherein the antimicrobial agent includes Rifampin and Minocycline.

43. The catheter kit according to claim 36, further comprising:
an anti-coagulant.

44. The catheter kit according to claim 43, wherein the anti-coagulant is heparin.

* * * * *